(12) United States Patent
Iwahara

(10) Patent No.: US 6,429,343 B1
(45) Date of Patent: Aug. 6, 2002

(54) PROCESS FOR PRODUCING BISPHENOL A

(75) Inventor: Masahiro Iwahara, Yamaguchi (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/926,047

(22) PCT Filed: Dec. 28, 2000

(86) PCT No.: PCT/JP00/09405

§ 371 (c)(1),
(2), (4) Date: Aug. 21, 2001

(87) PCT Pub. No.: WO01/49640

PCT Pub. Date: Jul. 12, 2001

(30) Foreign Application Priority Data

Jan. 7, 2000 (JP) ........................................ 2000-001824

(51) Int. Cl.⁷ ............................................... C07C 39/16
(52) U.S. Cl. ....................................... 568/728; 568/727
(58) Field of Search ................................. 568/727, 728

(56) References Cited

U.S. PATENT DOCUMENTS 4,859,803 A    8/1989   Shaw 5,315,042 A  *  5/1994   Cipullo

FOREIGN PATENT DOCUMENTS

| JP | 8-325185 | 12/1996 |
|---|---|---|
| JP | 11-246458 | 9/1999 |
| JP | 2000-128817 | 5/2000 |
| WO | WO 00/23408 | 4/2000 |

* cited by examiner

*Primary Examiner*—Michael L. Shippen
(74) *Attorney, Agent, or Firm*—Oblon, Spivak, McClelland, Maier & Neustadt, P.C.

(57) ABSTRACT

The present invention provides a process for producing bisphenol A which is capable of prolonging the life of an acid-type ion exchange resin partially modified with a sulfur-containing amine compound as catalyst, and increasing the yield of bisphenol A per unit quantity of the catalyst. There is disclosed a process for producing bisphenol A by reacting acetone with phenol in the presence of an acid-type ion exchange resin partially modified with a sulfur-containing amine compound as catalyst and alkylmercaptan as co-catalyst, said process comprising:

conducting said reaction using a multi-stage reaction apparatus comprising at least two individual reactors connected in series to each other, wherein the molar ratio of total alkylmercaptan to total acetone and the molar ratio of total acetone to phenol are increased as the conversion rate of the phenol is decreased.

10 Claims, No Drawings

PROCESS FOR PRODUCING BISPHENOL A

FIELD OF THE INVENTION

The present invention relates to a process for producing bisphenol A at a high yield per unit quantity of catalyst wherein an acid-type ion exchange resin as the catalyst which is partially modified with a sulfur-containing amine compound, exhibits a prolonged life. The thus produced bisphenol A is useful as raw materials of polycarbonate resins, epoxy resins, polyarylate resins and the like.

BACKGROUND ARTS

As well known in the arts, bisphenol A [2,2-bis(4-hydroxyphenyl) propane] is an important compound useful as raw materials of engineering plastics such as polycarbonate resins and polyarylate resins, or epoxy resins. Recently, the demand for the above compound tends to be more and more increased.

It is also known that bisphenol A is produced by reacting phenol with acetone in the presence of an acid-type ion exchange resin (acidic cation exchange resin) partially modified with a sulfur-containing amine compound as a catalyst together with alkylmercaptan as a co-catalyst (refer to Japanese Patent Laid-open No. 8-325185). However, the addition of alkylmercaptan solely fails to sufficiently prolong the life of the catalyst, and sufficiently increase a yield of bisphenol A per unit quantity of the catalyst. Also, there is known such a method in which the catalyst, when deteriorated in its catalytic activity, is regenerated by washing it with phenol or acidic solvents. However, the latter method suffers from problems such as low yield of the aimed product and complicated treatment of the waste solvents used for washing. Therefore, it has been required to develop a novel process for producing bisphenol A which is capable of not only prolonging the life of an acid-type ion exchange resin partially modified with a sulfur-containing amine compound as catalyst, but also increasing the yield of bisphenol A per unit quantity of the catalyst.

DISCLOSURE OF THE INVENTION

The present invention has been made in view of the above problems. An object of the present invention is to provide a process for producing bisphenol A which is capable of prolonging the life of an acid-type ion exchange resin partially modified with a sulfur-containing amine compound as catalyst, and increasing the yield of bisphenol A per unit quantity of the catalyst.

As a result of extensive studies, the inventors have found that the above object of the present invention is achieved by using a multi-stage reaction apparatus comprising at least two individual reactors connected in series to each other, and by increasing the molar ratio of total alkylmercaptan to total acetone and the molar ratio of total acetone to phenol as the conversion rate of phenol is decreased. The present invention has been accomplished based on this finding.

Thus, the present invention provides the following aspects:

(1) A process for producing bisphenol A by reacting acetone with phenol in the presence of an acid-type ion exchange resin partially modified with a sulfur-containing amine compound as catalyst together with alkylmercaptan as co-catalyst, said process comprising: conducting said reaction using a multi-stage reaction apparatus comprising at least two individual reactors connected in series to each other, in such a manner that the molar ratio of total alkylmercaptan to total acetone and the molar ratio of total acetone to phenol are increased as the conversion rate of the phenol is decreased;

(2) the process according to the above aspect (1) wherein whole amount of the phenol is fed into a first-stage reactor of said multi-stage reaction apparatus, and the acetone is fed in separate parts into the respective reactors of said multi-stage reaction apparatus;

(3) the process according to the above aspect (1) or (2) wherein the molar ratio of total acetone to phenol at an initial stage of the reaction is in the range of 1/9 to 1/11;

(4) the process according to any one of the above aspects (1) to (3) wherein the molar ratio of total alkyl mercaptan to total acetone and the molar ratio of total acetone to phenol are increased when the phenol conversion rate measured at an outlet of the last stage reactor of said multi-stage reaction apparatus is decreased to 90 to 99% of the initial phenol conversion rate;

(5) the process according to any one of the above aspects (1) to (4) wherein the molar ratio of total alkylmercaptan to total acetone is increased so as not to exceed 1/20;

(6) the process according to any one of the above aspects (1) to (5) wherein the molar ratio of total acetone to phenol is increased so as not to exceed 1/3;

(7) the process according to any one of the above aspects (1) to (6) wherein said sulfur-containing amine compound is selected from the group consisting of mercaptoalkyl amines and thiazolidines;

(8) the process according to any one of the above aspects (1) to (7) wherein said acid-type ion exchange resin is a sulfonic acid-type cation exchange resin;

(9) the process according to any one of the above aspects (1) to (8) wherein said alkylmercaptan is ethylmercaptan; and

(10) the process according to any one of the above aspects (1) to (9) wherein the reaction is conducted at a temperature of 60 to 100° C.

DESCRIPTION OF THE PREFERRED EMBODIMENTS

The present invention will be described in detail below.

First, the respective steps of the process for the production of bisphenol A are described.

Step (1): Reaction Step

Bisphenol A is produced by reacting acetone with an excess amount of phenol in the presence of an acid-type ion exchange resin as catalyst and alkyl mercaptan as co-catalyst. As the suitable acid-type ion exchange resins as catalyst, there may be generally used sulfonic acid-type cation exchange resins. Examples of such acid-type ion exchange resin include sulfonated styrene-divinyl benzene copolymers, sulfonated cross-linked styrene polymers, phenol formaldehyde-sulfonic acid resins, benzene formaldehyde-sulfonic acid resins or the like. These acid-type ion exchange resins may be used alone or in the form of a mixture of any two or more thereof.

As the sulfur-containing amine compounds used to partially modify the acid-type ion exchange resin, there may be used mercaptoalkyl amines such as 2-mercaptoethyl amine and 3-mercaptobutyl amine; thiazolidines such as 2,2-dimethyl thiazolidine, 2-methyl-2-ethyl thiazolidine, cycloalkyl thiazolidines, 2-methyl-2-phenyl thiazolidine and 3-methyl thiazolidine; aminothiophenols such as 1,4-aminothiophenol; mercaptoalkyl pyridines such as 3-mercaptomethyl pyridine, 3-mercaptoethyl pyridine and 4-mercaptoethyl pyridine; and the like. Among these sulfur-containing amine compounds, mercaptoalkyl amines and thiazolidines are preferred. The amount of the sulfur-containing amine compound used for modifying the acid-type ion exchange resin is preferably 2 to 50 mol %, more preferably 5 to 30 mol % based on a sulfonic group contained in the acid-type ion exchange resin.

The acid-type ion exchange resin may be modified by reacting the resin with the sulfur-containing amine compound in water or an organic solvent. As the organic solvents, there may be used phenol, acetone, methanol or the like. The modification reaction is preferably conducted in water. The reaction may also be conducted at ordinary temperature or under heated condition. It is not required to conduct the reaction for a too long period of time, and the modification of the acid-type ion exchange resin is sufficiently completed by conducting the above reaction for several tens minutes. The reaction mixture is preferably stirred for uniform reaction thereof The suitable alkylmercaptans used as co-catalyst are such mercaptans having a $C_1$–$C_{10}$ alkyl group. Examples of the alkylmercaptans include methylmercaptan, ethylmercaptan, propylmercaptan, octylmercaptan, cyclohexylmercaptan or the like. Among these alkylmercaptans, ethylmercaptan is especially preferred. Meanwhile, these alkylmercaptans may be used alone or in the form of a mixture of any two or more thereof.

The resultant reaction mixture contains, in addition to bisphenol A, unreacted phenol, unreacted acetone, by-produced water, alkylmercaptan, and other by-products such as organic sulfur compounds and colored substances.

Step (2): Recovery of By-produced Water and Unreacted Raw Materials

Then, the reaction mixture obtained in the step (1) is distilled under reduced pressure to remove unreacted acetone, by-produced water, alkylmercaptan, etc., from a top of distillation column and obtain a liquid mixture containing bisphenol A, phenol, etc., from the bottom thereof. The reduced-pressure distillation may be conducted at a temperature of 70 to 180° C. under a pressure of 6.7 to 80.0 kPa. Upon such a distillation, the unreacted phenol is subjected to azeotropy, and removed out of the reaction system from the top of the distillation column.

Step (3): Concentration of Bisphenol A

The bottoms obtained by distilling off the above substances from the reaction mixture, is further distilled under reduced pressure to remove unreacted phenol therefrom and concentrate bisphenol A contained therein. The thus obtained concentrated residual solution is used as raw material of the subsequent crystallization step. The concentration conditions are not particularly restricted, but the concentration step may be usually conducted at a temperature of 100 to 170° C. under a pressure of 5.3 to 66.7 kPa. When the temperature is less than 100° C., it is necessary to keep the reaction system under high vacuum condition. On the contrary, when the temperature is more than 170° C., an additional heat-removal step is required upon conducting the subsequent crystallization step. The concentration of bisphenol A contained in the concentrated residual solution is in the range of 20 to 50% by weight, preferably 20 to 40% by weight. When the concentration of bisphenol A contained in the concentrated residual solution is less than 20% by weight, the recovery percentage of bisphenol A becomes lowered. On the contrary, when the concentration of bisphenol A in the residual solution is more than 50% by weight, it is difficult to transport a slurry obtained after the crystallization step.

Step (4): Crystallization

The concentrated residual solution obtained in the step (3) is cooled to 40 to 70° C. to crystallize an adduct of bisphenol A and phenol (hereinafter referred to merely as "phenol adduct"), thereby obtaining a slurry. The cooling is conducted due to heat removal caused by evaporating water added to external heat exchanger or crystallizer. Next, the slurry-like concentrated residual solution is subjected to filtration, centrifugal separation, etc., and separated into the phenol adduct and a crystallization mother liquor containing the by-products. The obtained crystallization mother liquor may be wholly or partially recycled to the multi-stage reaction apparatus, or recovered as phenol or isopropenyl phenol by subjecting whole or part thereof to alkali decomposition. Alternatively, whole or part of the crystallization mother liquor may be isomerized and recycled as raw material to the crystallization step (refer to Japanese Patent Laid-open No. 6-321834).

Step (5): Heat-melting of Phenol Adduct

The 1:1 adduct of bisphenol A and phenol obtained in the step (4) in the form of crystals, is heat-melted at a temperature of 100 to 160° C. to obtain a liquid mixture.

Step (6): Recovery of Bisphenol A

The liquid mixture obtained in the step (5) is distilled under reduced pressure to remove phenol and recover bisphenol A therefrom. The reduced-pressure distillation is conducted at a temperature of 150 to 190° C. under a pressure of 1.3 to 13.3 kPa. In addition, the removal of residual phenol may be conducted by known methods such as steam-stripping.

Step (7): Granulation of Bisphenol A

The molten bisphenol A obtained in the step (6) is formed into droplets using a granulating apparatus such as spray dryer, and cooled and solidified to obtain an aimed product. The droplets are produced by spraying, spreading or the like method, and then cooled with nitrogen, air or the like.

Next, the process of the present invention will be described in detail below.

In the process of the present invention, a multi-stage reaction apparatus comprising at least two individual reactors connected in series to each other is used in the step (1), and the molar ratio of total alkylmercaptan to total acetone and the molar ratio of total acetone to phenol are increased as the conversion rate of the phenol is decreased. The two molar ratios may be increased continuously or stepwise.

As the reaction apparatus, there is used a multi-stage reaction apparatus which comprises at least two individual or discrete reactors connected in series to each other. The production of bisphenol A is conducted by exothermic reaction. Therefore, when a single reactor is used, the reactor is required to have a complicated structure for removing the heat of reaction. If no means for heat removal is provided in the reactor, there arises such an inconvenience that temperature rise as high as about 10 to 20° C. is caused, so that the temperature of the reactor far exceeds the temperature suitable for using the ion exchange resin therein, or the temperature range of 55 to 95° C. in which bisphenol A is appropriately produced.

Upon operation of the above multi-stage reaction apparatus, in view of the life of the catalyst used therein, it is preferred that whole amount of the phenol is charged into the first reactor thereof, and the acetone is charged in separate parts into the respective reactors thereof. Meanwhile, the alkylmercaptan may be wholly charged into the first reactor, or may be charged in separated parts into the respective reactors.

The reaction temperature in the respective reactors of the multi-stage reaction apparatus is preferably in the range of 60 to 100° C. When the reaction temperature is too low, the phenol phase tends to be solidified. On the contrary, when the reaction temperature is too high, the ion exchange resin tends to be considerably deteriorated. The reaction temperature is more preferably in the range of 65 to 95° C.

At an initial stage of the reaction, the molar ratio of total acetone to phenol is preferably in the range of 1/9 to 1/11. When the molar ratio of total acetone to phenol is more than 1/9, undesirable side reactions between acetone and phenol tend to occur. On the contrary, when the molar ratio of total acetone to phenol is less than 1/11, the conversion rate based on phenol tends to be lowered, resulting in increased amount of phenol recovered and low yield of the aimed bisphenol A.

In the present invention, it is required that when the phenol conversion rate measured at an outlet of the last stage reactor of the multi-stage reaction apparatus is decreased to 90 to 99% of the initial conversion rate, the molar ratio of total alkylmercaptan to total acetone and the molar ratio of total acetone to phenol are increased. In this case, the molar ratio of total alkylmercaptan to total acetone is increased so as not to exceed 1/20, and the molar ratio of total acetone to phenol is increased so as not to exceed 1/3. When each of the molar ratios exceeds the above-specified limit, undesirable side reactions tend to frequently occur.

Meanwhile, the alkylmercaptan may be added at an initial stage of the reaction or at the time at which the phenol conversion rate begins to be decreased.

In the present invention, the reaction is continued until the molar ratio of total alkylmercaptan to total acetone reaches 1/20, or the molar ratio of total acetone to phenol reaches 1/3. Upon reaching either one of the molar ratios, the catalyst is replaced with new one.

The present invention will be described more specifically by reference to the following examples. However, these examples are only illustrative and not intended to limit the present invention thereto.

EXAMPLE 1

Two packed bed-type reactors each having an inner diameter of 13 mm and a height of 561 mm, were respectively filled with a sulfonic acid-type cation exchange resin 20% of which was modified with 2-mercaptoethyl amine (74.4 ml in phenol-wetted state; "DIAION SK- 104 H" available from Mitsubishi Chemical Corp.) and connected in series to each other.

Phenol was passed through the first-stage reactor at a feed rate of 4.68 moles per hour, and acetone was passed through both the first- and second-stage reactors at a feed rate of 0.234 mole per hour (molar ratio of acetone to phenol: 1/20; molar ratio of total acetone to phenol: 1/10). The reaction was conducted in the reactors while maintaining the reaction temperature thereof at 75° C. The resultant reaction mixture was periodically analyzed with time to determine a phenol conversion rate.

As a result, it was confirmed that at the beginning of the reaction, the phenol conversion rates of the first- and second-stage reactors were 6.0% and 10.6%, respectively.

(1) After 600 hours, the phenol conversion rates of the first- and second-stage reactors were decreased to 4.8% and 9.7%, respectively. At this time, ethylmercaptan-containing acetone was supplied instead of acetone at the following molar ratio to the first- and second-stage reactors, and further the molar ratio of acetone to phenol was increased as follows.

Molar ratio of ethylmercaptan to acetone: 1/1,000

Molar ratio of acetone to phenol: 1.05/20 (Molar ratio of total acetone to phenol: 1.05/10)

After the reaction conditions were changed as described above, it was confirmed that the phenol conversion rates of the first- and second-stage reactors were increased to 5.9% and 10.7%, respectively.

(2) After 1,300 hours, the phenol conversion rates of the first- and second-stage reactors were decreased to 4.6% and 9.3%, respectively. At this time, the molar ratio of ethylmercaptan to acetone and the molar ratio of acetone to phenol in the first- and second-stage reactors were respectively increased as follows.

Molar ratio of ethylmercaptan to acetone: 1/800

Molar ratio of acetone to phenol: 1.11/20 (Molar ratio of total acetone to phenol: 1.11/10)

After the reaction conditions were changed as described above, it was confirmed that the phenol conversion rates of the first- and second-stage reactors were increased to 6.1% and 10.6%, respectively.

(3) After 2,000 hours, the phenol conversion rates of the first- and second-stage reactors were decreased to 4.3% and 9.1%, respectively. At this time the molar ratio of ethylmercaptan to acetone and the molar ratio of acetone to phenol in the first- and second-stage reactors were respectively increased as follows.

Molar ratio of ethylmercaptan to acetone: 1/600

Molar ratio of acetone to phenol: 1.18/20 Molar ratio of total acetone to phenol: 1.18/10)

After the reaction conditions were changed as described above, it was confirmed that the phenol conversion rates of the first- and second-stage reactors were increased to 6.0% and 10.8%, respectively.

(4) After 2,800 hours, the phenol conversion rates of the first- and second-stage reactors were decreased to 4.2% and 9.3%, respectively. At this time, the molar ratio of ethylmercaptan to acetone and the molar ratio of acetone to phenol in the first- and second-stage reactors were respectively increased as follows.

Molar ratio of ethylmercaptan to acetone: 1/400

Molar ratio of acetone to phenol: 1.25/20 (Molar ratio of total acetone to phenol: 1.25/10)

After the reaction conditions were changed as described above, it was confirmed that the phenol conversion rates of the first- and second-stage reactors were increased to 5.8% and 10.7%, respectively.

(5) After 3,600 hours, the phenol conversion rates of the first- and second-stage reactors were decreased to 4.5% and 9.4%, respectively. At this time, the molar ratio of ethylmercaptan to acetone and the molar ratio of acetone to phenol in the first- and second-stage reactors were respectively increased as follows.

Molar ratio of ethylmercaptan to acetone: 1/200

Molar ratio of acetone to phenol: 1.31/20 (Molar ratio of total acetone to phenol: 1.31/10)

After the reaction conditions were changed as described above, it was confirmed that the phenol conversion rates of the first- and second-stage reactors were increased to 6.2% and 10.8%, respectively.

(6) After 4,800 hours, the phenol conversion rates of the first- and second-stage reactors were decreased to 4.1% and 9.2%, respectively. At this time, the molar ratio of ethylmercaptan to acetone and the molar ratio of acetone to phenol in the first- and second-stage reactors were respectively increased as follows.

Molar ratio of ethylmercaptan to acetone: 1/100

Molar ratio of acetone to phenol: 1.39/20 (Molar ratio of total acetone to phenol: 1.39/10)

After the reaction conditions were changed as described above, it was confirmed that the phenol conversion rates of the first- and second-stage reactors were increased to 6.0% and 10.6%, respectively.

(7) After 5,700 hours, the phenol conversion rates of the first- and second-stage reactors were decreased to 3.9% and 9.0%, respectively. At this time, the molar ratio of ethylmercaptan to acetone and the molar ratio of acetone to phenol in the first- and second-stage reactors were respectively increased as follows.

Molar ratio of ethylmercaptan to acetone: 1/70

Molar ratio of acetone to phenol: 1.47/20 (Molar ratio of total acetone to phenol: 1.47110)

After the reaction conditions were changed as described above, it was confirmed that the phenol conversion rates of the first- and second-stage reactors were increased to 5.8% and 10.4%, respectively.

(8) After 6,800 hours, the phenol conversion rates of the first- and second-stage reactors were decreased to 3.8% and 8.8%, respectively. At this time, the molar ratio of ethylmercaptan to acetone and the molar ratio of acetone to phenol in the first- and second-stage reactors were respectively increased as follows.

Molar ratio of ethylmercaptan to acetone: 1/40

Molar ratio of acetone to phenol: 1.55/20 (Molar ratio of total acetone to phenol: 1.55/10)

After the reaction conditions were changed as described above, it was confirmed that the phenol conversion rates of the first- and second-stage reactors were increased to 5.7% and 10.5%, respectively.

Further, it was also confirmed that the selectivity of bisphenol A was maintained in the range of 94.0 to 94.5% for a period of from the beginning of the reaction up to the elapse of 6,800 hours.

EXAMPLE 2

The same procedure as in EXAMPLE 1 was repeated except that 2,2-dimethyl thiazolidine was used instead of 2-mercaptoethyl amine, and three packed bed-type reactors were used instead of the two reactors such that acetone was passed through each of the first- to third-stage reactors at a feed rate of 0.156 mole per hour (molar ratio of acetone to phenol: 1/30; molar ratio of total acetone to phenol: 1/10). The resultant reaction mixture was periodically analyzed with time to determine a phenol conversion rate.

It was confirmed that at the beginning of the reaction, the phenol conversion rates of the first-, second- and third-stage reactors were 6.0%, 10.4% and 14.2%, respectively.

(1) After 900 hours, the phenol conversion rates of the first-, second-and third-stage reactors were decreased to 4.3%, 9.4% and 13.9%, respectively. At this time, ethylmercaptan-containing acetone was supplied instead of acetone at the following molar ratio to the first-stage reactor, and further the molar ratio of acetone to phenol at each of the first- to third-stage reactors was increased as follows.

Molar ratio of ethylmercaptan to acetone: 1/1,100

Molar ratios of acetone to phenol: 1.04/30 (Molar ratio of total acetone to phenol: 1.04/10)

After the reaction conditions were changed as described above, it was confirmed that the phenol conversion rates of the first-, second- and third-stage reactors were increased to 5.9%, 10.6% and 13.9%, respectively.

(2) After 1,900 hours, the phenol conversion rates of the first-, second-and third-stage reactors were decreased to 4.1%, 9.1% and 13.5%, respectively. At this time, the molar ratio of ethylmercaptan to acetone fed to the first-stage reactor, and the molar ratio of acetone to phenol at each of the first- to third-stage reactors were respectively increased as follows.

Molar ratio of ethylmercaptan to acetone: 1/800

Molar ratios of acetone to phenol: 1.15/30 (Molar ratio of total acetone to phenol: 1.15/10)

After the reaction conditions were changed as described above, it was confirmed that the phenol conversion rates of the first-, second- and third-stage reactors were increased to 5.8%, 10.4% and 14.2%, respectively.

(3) After 3,000 hours, the phenol conversion rates of the first-, second-and third-stage reactors were decreased to 4.0%, 9.0% and 13.3%, respectively. At this time, the molar ratio of ethylmercaptan to acetone fed to the first-stage reactor, and the molar ratio of acetone to phenol at each of the first- to third-stage reactors were respectively increased as follows.

Molar ratio of ethylmercaptan to acetone: 1/400

Molar ratios of acetone to phenol: 1.26/30 (Molar ratio of total acetone to phenol: 1.26/10)

After the reaction conditions were changed as described above, it was confirmed that the phenol conversion rates of the first-, second- and third-stage reactors were increased to 5.7%, 10.2% and 14.1%, respectively.

(4) After 4,200 hours, the phenol conversion rates of the first-, second-and third-stage reactors were decreased to 3.8%, 8.7% and 12.9%, respectively. At this time, the molar ratio of ethylmercaptan to acetone fed to the first-stage reactor and the molar ratio of acetone to phenol at each of the first- to third-stage reactors were respectively increased as follows.

Molar ratio of ethylmercaptan to acetone: 1/200

Molar ratios of acetone to phenol: 1.57/30 (Molar ratio of total acetone to phenol: 1.57/10)

After the reaction conditions were changed as described above, it was confirmed that the phenol conversion rates of the first-, second- and third-stage reactors were increased to 5.8%, 10.3% and 14.3%, respectively.

(5) After 5,500 hours, the phenol conversion rates of the first-, second-and third-stage reactors were decreased to 3.3%, 7.8% and 12.2%, respectively. At this time, the molar ratio of ethylmercaptan to acetone fed to the first-stage reactor and the molar ratio of acetone to phenol at each of the first- to third-stage reactors, were respectively increased as follows.

Molar ratio of ethylmercaptan to acetone: 1/100

Molar ratios of acetone to phenol: 1.84/30 (Molar ratio of total acetone to phenol: 1.84/10)

After the reaction conditions were changed as described above, it was confirmed that the phenol conversion rates of the first-, second- and third-stage reactors were increased to 5.6%, 10.1% and 14.2%, respectively.

(6) After 6,500 hours, the phenol conversion rates of the first-, second-and third-stage reactors were decreased to 2.9%, 7.1% and 11.9%, respectively. At this time, the molar ratio of ethylmercaptan to acetone fed to the first-stage reactor and the molar ratio of acetone to phenol at each of the first- to third-stage reactors, were respectively increased as follows.

Molar ratio of ethylmercaptan to acetone: 1/40

Molar ratios of acetone to phenol: 2.26/30 (Molar ratio of total acetone to phenol: 2.26/10)

After the reaction conditions were changed as described above, it was confirmed that the phenol conversion rates of the first-, second- and third-stage reactors were increased to 5.3%, 9.7% and 14.1%, respectively.

Further, it was also confirmed that the selectivity of bisphenol A was maintained in the range of 94.1 to 94.5% for a period of from the beginning of the reaction up to the elapse of 6,500 hours.

COMPARATIVE EXAMPLE 1

The same procedure as in EXAMPLE 1 was repeated except that the two reactors having a height of 561 mm as used in EXAMPLE 1 were replaced with one reactor having a height of 1,122 mm, and acetone was fed to the reactor at a feed rate of 0.468 mole per hour (molar ratio of acetone to phenol: 1/10).

The resultant reaction mixture was periodically analyzed with time to determine a phenol conversion rate.

It was confirmed that the phenol conversion rate at the beginning of the reaction was 10.6%.

(1) After 800 hours, the phenol conversion rate was decreased to 9.2%. At this time, ethylmercaptan-containing acetone was fed to the reactor instead of acetone (molar ratio of ethylmercaptan to acetone: 1/500). After the reaction conditions were changed as described above, it was confirmed that the phenol conversion rate was 10.5%.

(2) After 1,600 hours, the phenol conversion rate was decreased to 8.5%. At this time, the ethylmercaptan concentration was increased such that the molar ratio of ethylmercaptan to acetone was 1/100. After the reaction conditions were changed as described above, it was confirmed that the phenol conversion rate was 10.2%.

(3) After 2,200 hours, the phenol conversion rate was decreased to 7.8%. At this time, the ethylmercaptan concentration was increased such that the molar ratio of ethylmercaptan to acetone was 1/50. After the reaction conditions were changed as described above, it was confirmed that the phenol conversion rate was 10.0%.

(4) After 2,900 hours, the phenol conversion rate was decreased to 7%. At this time, the ethylmercaptan concentration was increased such that the molar ratio of ethylmercaptan to acetone was 1/120. After the reaction conditions were changed as described above, it was confirmed that the phenol conversion rate was 9.7%.

(5) After 3,400 hours, the phenol conversion rate was decreased to 6.6%. At this time, the ethylmercaptan concentration was increased such that the molar ratio of ethylmercaptan to acetone was 1/15. After the reaction conditions were changed as described above, it was confirmed that the phenol conversion rate was 9.1%.

(6) After 4,100 hours, the phenol conversion rate was decreased to 5.1%. At this time, the ethylmercaptan concentration was increased such that the molar ratio of ethylmercaptan to acetone was 1/10. After the reaction conditions were changed as described above, it was confirmed that the phenol conversion rate was 8.6%.

(7) After 4,800 hours, the phenol conversion rate was decreased to 4.5%. At this time, the ethylmercaptan concentration was increased such that the molar ratio of ethylmercaptan to acetone was 1/7. After the reaction conditions were changed as described above, it was confirmed that the phenol conversion rate was 7.3%.

COMPARATIVE EXAMPLE 2

The same procedure as in EXAMPLE 1 was repeated except that the two reactors each having a height t of 561 mm as us ed in EXAMPLE 1 were replaced with two reactors each having a height of 1,122 mm, and acetone was fed to each reactor at a feed rate of 0.468 mole per hour (molar ratio of acetone to phenol: 1/10).

The resultant reaction mixture was periodically analyzed with time to determine a phenol conversion rate.

It was confirmed that the phenol conversion rate at the beginning of the reaction was 10.6%.

(1) After 800 hours, the phenol conversion rate was decreased to 9.2%. At this time, the acetone concentration was increased such that the molar ratio of acetone to phenol was 1.21/10. After the reaction conditions were changed as described above, it was confirmed that the phenol conversion rate was 10.5%.

(2) After 1, 500 hours, the phenol conversion rate was decreased to 8.9%. At this time, the acetone concentration was increased such that the molar ratio of acetone to phenol was 1.42/10. After the reaction conditions were changed as described above, it was confirmed that the phenol conversion rate was 10.6%.

(3) After 2,200 hours, the phenol conversion rate was decreased to 8.1%. At this time, the acetone concentration was increased such that the molar ratio of acetone to phenol was 1.63/10. After the reaction conditions were changed as described above, it was confirmed that the phenol conversion rate was 10.2%.

(4) After 3,000 hours, the phenol conversion rate was decreased to 7.7%. At this time, the acetone concentration was increased such that the molar ratio of acetone to phenol was 1.92/10. After the reaction conditions were changed as described above, it was confirmed that the phenol conversion rate was 9.9%.

(5) After 3,500 hours, the phenol conversion rate was decreased to 7.0%. At this time, the acetone concentration was increased such that the molar ratio of acetone to phenol was 2.22/10. After the reaction conditions were changed as described above, it was confirmed that the phenol conversion rate was 9.3%.

(6) After 4,000 hours, the phenol conversion rate was decreased to 6.7%. At this time, the acetone concentration was increased such that the molar ratio of acetone to phenol was 2.56/10. After the reaction conditions were changed as described above, it was confirmed that the phenol conversion rate was 8.7%.

From the above-mentioned EXAMPLES and COMPARATIVE EXAMPLES, it is recognized that the life of the catalyst used is considerably prolonged by using such a multi-stage reaction apparatus comprising at least two individual reactors and by increasing the molar ratio of alkylmercaptan to acetone and the molar ratio of acetone to phenol as the phenol conversion rate is decreased.

INDUSTRIAL APPLICABILITY

In accordance with the process of the present invention, the acid-type ion exchange resin partially modified with a sulfur-containing amine compound as catalyst, exhibits a prolonged life, and the yield of bisphenol A per unit quantity of the catalyst is increased.

What is claimed is:

1. A process for producing bisphenol A by reacting acetone with phenol in the presence of an acid-type ion exchange resin partially modified with a sulfur-containing amine compound as catalyst and alkylmercaptan as co-catalyst, said process comprising:

conducting said reaction using a multi-stage reaction apparatus comprising at least two individual reactors connected in series to each other, wherein the molar ratio of total alkylmercaptan to total acetone and the molar ratio of total acetone to phenol are increased as the conversion rate of the phenol is decreased.

2. A process according to claim 1, wherein whole amount of the phenol is fed into a first-stage reactor of the multi-stage reaction apparatus, and the acetone is fed in separate parts into the respective reactors.

3. A process according to claim 1, wherein the molar ratio of total acetone to phenol at an initial stage of the reaction is in the range of 1/9 to 1/11.

4. A process according to claim 1, wherein the molar ratio of total alkyl mercaptan to total acetone and the molar ratio of total acetone to phenol are increased when the phenol conversion rate measured at an outlet of the last stage reactor of said multi-stage reaction apparatus is decreased to 90 to 99% of the initial conversion rate.

5. A process according to claim 1, wherein the molar ratio of total alkyl mercaptan to total acetone is increased so as not to exceed 1/20.

6. A process according to claim 1, wherein the molar ratio of total acetone to phenol is increased so as not to exceed 1/3.

7. A process according to claim 1, wherein said sulfur-containing amine compound is selected from the group consisting of mercaptoalkyl amines and thiazolidines.

8. A process according to claim 1, wherein said acid-type ion exchange resin is a sulfonic acid-type cation exchange resin.

9. A process according to claim 1, wherein said alkylmercaptan is ethylmercaptan.

10. A process according to claim 1, wherein the reaction is conducted at a temperature of 60 to 100° C.

* * * * *